United States Patent
Jones

(10) Patent No.: US 6,307,073 B1
(45) Date of Patent: Oct. 23, 2001

(54) DIRECT EPOXIDATION PROCESS USING A MIXED CATALYST SYSTEM

(75) Inventor: C. Andrew Jones, Newtown Square, PA (US)

(73) Assignee: ARCO Chemical Technology, L.P., Greenville, DE (US)

( * ) Notice: Subject to any disclaimer, the term of this patent is extended or adjusted under 35 U.S.C. 154(b) by 0 days.

(21) Appl. No.: 09/624,942

(22) Filed: Jul. 25, 2000

(51) Int. Cl.[7] .................................................. C07D 301/06
(52) U.S. Cl. ........................ 549/532; 549/523; 549/524
(58) Field of Search ................................. 549/532, 523, 549/524; 502/71, 64, 69, 242, 243

(56) References Cited

U.S. PATENT DOCUMENTS

| | | | |
|---|---|---|---|
| 3,351,635 | 11/1967 | Kollar | 260/348.5 |
| 4,367,342 | 1/1983 | Wulff et al. | 549/529 |
| 4,410,501 | 10/1983 | Taramasso et al. | 423/326 |
| 4,833,260 | 5/1989 | Neri et al. | 549/531 |
| 5,623,090 | 4/1997 | Haruta et al. | 568/360 |
| 6,005,123 | * 12/1999 | Dessau et al. | 549/531 |
| 6,008,388 | * 12/1999 | Dessau et al. | 549/531 |
| 6,008,389 | * 12/1999 | Grosch et al. | 549/533 |
| 6,031,116 | * 2/2000 | Bowman et al. | 549/523 |
| 6,063,942 | * 5/2000 | Grey | 549/523 |
| 6,106,797 | * 8/2000 | Muller et al. | 423/584 |

FOREIGN PATENT DOCUMENTS

| | | |
|---|---|---|
| 1001038A7 | 6/1989 | (BE) . |
| 4-352771 | 12/1992 | (JP) . |
| WO 98/00413 | 1/1998 | (WO) . |

\* cited by examiner

*Primary Examiner*—Rosalynd Keys
(74) *Attorney, Agent, or Firm*—Kevin M. Carroll

(57) ABSTRACT

A catalyst mixture containing a titanium zeolite and a supported gold-containing catalyst is highly selective and productive for transforming olefins to epoxides in the liquid-phase reaction of an olefin, hydrogen, and oxygen. This is particularly surprising because neither titanium zeolite nor the supported gold-containing catalyst alone is effective in olefin epoxidation.

13 Claims, No Drawings

DIRECT EPOXIDATION PROCESS USING A MIXED CATALYST SYSTEM

FIELD OF THE INVENTION

This invention relates to a liquid-phase epoxidation process using a mixed catalyst system to produce epoxides from hydrogen, oxygen, and olefins. The mixed catalyst system contains a titanium zeolite and a gold-containing supported catalyst. Surprisingly, this reaction is performed in the absence of palladium, which has typically been required in previous liquid-phase direct oxidation processes.

BACKGROUND OF THE INVENTION

Many different methods for the preparation of epoxides have been developed. Generally, epoxides are formed by the reaction of an olefin with an oxidizing agent in the presence of a catalyst. The production of propylene oxide from propylene and an organic hydroperoxide oxidizing agent, such as ethyl benzene hydroperoxide or tert-butyl hydroperoxide, is commercially practiced technology. This process is performed in the presence of a solubilized molybdenum catalyst, see U.S. Pat. No. 3,351,635, or a heterogeneous titania on silica catalyst, see U.S. Pat. No. 4,367,342. Hydrogen peroxide is another oxidizing agent useful for the preparation of epoxides. Olefin epoxidation using hydrogen peroxide and a titanium silicate zeolite is demonstrated in U.S. Pat. No. 4,833,260. One disadvantage of both of these processes is the need to pre-form the oxidizing agent prior to reaction with olefin.

Another commercially practiced technology is the direct epoxidation of ethylene to ethylene oxide by reaction with oxygen over a silver catalyst. Unfortunately, the silver catalyst has not proved very useful in epoxidation of higher olefins. Therefore, much current research has focused on the direct epoxidation of higher olefins with oxygen and hydrogen in the presence of a catalyst. In this process, it is believed that oxygen and hydrogen react in situ to form an oxidizing agent. Thus, development of an efficient process (and catalyst) promises less expensive technology compared to the commercial technologies that employ pre-formed oxidizing agents.

Many different catalysts have been proposed for use in the direct epoxidation of higher olefins. For liquid-phase reactions, the catalysts typically contain palladium which promotes the formation of the in situ oxidizing agent. For example, JP 4-352771 discloses the epoxidation of propylene oxide from the reaction of propylene, oxygen, and hydrogen using a catalyst containing a Group VIII metal such as palladium on a crystalline titanosilicate. The vapor-phase oxidation of olefins has been shown to produce epoxides over gold supported on titanium oxide (Au/$TiO_2$ or Au/$TiO_2$-$SiO_2$), see for example U.S. Pat. No. 5,623,090, and gold supported on titanosilicates, see for example PCT Intl. Appl. WO 98/00413. U.S. Pat. No. 5,623,090 also demonstrates that the Au/$TiO_2$-$SiO_2$ catalyst is useful for the epoxidation of olefins in hydrocarbon solvents such as benzene (see Example 7).

One disadvantage of the described direct epoxidation catalysts is that they all show either less than optimal selectivity or productivity. As with any chemical process, it is desirable to develop new direct epoxidation methods and catalysts.

I have discovered an effective, convenient epoxidation process using a mixed catalyst system that gives good productivity and selectivity to epoxide.

SUMMARY OF THE INVENTION

The invention is an olefin epoxidation process that comprises reacting an olefin, oxygen, and hydrogen in an oxygenated solvent in the presence of a catalyst mixture comprising a titanium zeolite and a supported gold-containing catalyst. Although neither of the catalysts alone produce epoxide, it is surprisingly found that the catalyst mixture produces epoxide with high selectivity and productivity.

DETAILED DESCRIPTION OF THE INVENTION

The process of the invention employs a catalyst mixture that comprises a titanium zeolite and a supported catalyst comprising gold and a support. Suitable titanium zeolites are those crystalline materials having a porous molecular sieve structure with titanium atoms substituted in the framework. The choice of titanium zeolite employed will depend upon a number of factors, including the size and shape of the olefin to be epoxidized. For example, it is preferred to use a relatively small pore titanium zeolite such as a titanium silicalite if the olefin is a lower aliphatic olefin such as ethylene, propylene, or 1-butene. Where the olefin is propylene, the use of a TS-1 titanium silicalite is especially advantageous. For a bulky olefin such as cyclohexene, a larger pore titanium zeolite such as a titanium zeolite having a structure isomorphous with zeolite beta may be preferred.

Titanium zeolites comprise the class of zeolitic substances wherein titanium atoms are substituted for a portion of the silicon atoms in the lattice framework of a molecular sieve. Such substances are well known in the art.

Particularly preferred titanium zeolites include the class of molecular sieves commonly referred to as titanium silicalites, particularly "TS-1" (having an MFI topology analogous to that of the ZSM-5 aluminosilicate zeolites), "TS-2" (having an MEL topology analogous to that of the ZSM-11 aluminosilicate zeolites), and "TS-3" (as described in Belgian Pat. No. 1,001,038). Titanium-containing molecular sieves having framework structures isomorphous to zeolite beta, mordenite, ZSM-48, ZSM-12, and MCM-41 are also suitable for use. The titanium zeolites preferably contain no elements other than titanium, silicon, and oxygen in the lattice framework, although minor amounts of boron, iron, aluminum, sodium, potassium, copper and the like may be present.

Preferred titanium zeolites will generally have a composition corresponding to the following empirical formula $xTiO_2$ $(1-x)SiO_2$ where x is between 0.0001 and 0.5000. More preferably, the value of x is from 0.01 to 0.125. The molar ratio of Si:Ti in the lattice framework of the zeolite is advantageously from 9.5:1 to 99:1 (most preferably from 9.5:1 to 60:1). The use of relatively titanium-rich zeolites may also be desirable.

The catalyst mixture employed in the process of the invention also contains a supported catalyst comprising gold and a support. The support is an inorganic oxide that contains titanium or zirconium. The amount of titanium or zirconium present in the support is preferably in the range of from about 0.1 to about 75 weight percent. Preferred supports include titania, zirconia, amorphous titania-silica, Ti/MCM-41, Ti-MCM-48, Ti/SBA-15, and ETS-10.

The supported catalyst useful in the process of the invention also contains gold. The typical amount of gold present in the catalyst will be in the range of from about 0.01 to 20 weight percent, preferably 0.01 to 10 weight percent, and most preferably 0.01 to 5 weight percent. While various methods known to those skilled in the art may be used, preferably the gold may be supported by a deposition-precipitation method in which a gold compound is deposited and precipitated on the surface of the support by controlling the pH and temperature of the aqueous gold solution (as described in U.S. Pat. No. 5,623,090).

There are no particular restrictions regarding the choice of gold compound used in the preparation of the supported catalyst. For example, suitable compounds include gold halides (e.g., chlorides, bromides, iodides), cyanides, and sulfides. Chloroauric acid is particularly useful.

The titanium zeolite and the supported catalyst may be used in the epoxidation process as a mixture of powders or as a mixture of pellets. In addition, the titanium zeolite and supported catalyst may also be pelletized or extruded together prior to use in epoxidation. If pelletized or extruded together, the catalyst mixture may additionally comprise a binder or the like and may be molded, spray dried, shaped or extruded into any desired form prior to use in epoxidation. The weight ratio of titanium zeolite:supported catalyst is not particularly critical. However, a titanium zeolite:supported catalyst ratio of 0.01–100 (grams of titanium zeolite per gram of supported catalyst) is preferred.

The process of the invention comprises contacting an olefin, oxygen, and hydrogen in an oxygenated solvent in the presence of the catalyst mixture. Suitable olefins include any olefin having at least one carbon-carbon double bond, and generally from 2 to 60 carbon atoms. Preferably the olefin is an acyclic alkene of from 2 to 30 carbon atoms; the process of the invention is particularly suitable for epoxidizing $C_2$–$C_6$ olefins. More than one double bond may be present, as in a diene or triene for example. The olefin may be a hydrocarbon (i.e., contain only carbon and hydrogen atoms) or may contain functional groups such as halide, carboxyl, hydroxyl, ether, carbonyl, cyano, or nitro groups, or the like. The process of the invention is especially useful for converting propylene to propylene oxide.

The process of the invention also requires the use of an oxygenated solvent. Oxygenated solvents may be any chemical that is a liquid under reaction conditions that contains at least one oxygen atom in its chemical structure. Suitable oxygenated solvents include water and oxygen-containing hydrocarbons such as alcohols, ethers, esters, ketones, and the like. Preferred oxygenated solvents include lower aliphatic $C_1$–$C_4$ alcohols such as methanol, ethanol, isopropanol, and tert-butanol, or mixtures thereof, and water. Fluorinated alcohols can be used. It is also possible to use mixtures of the cited alcohols with water. If water or a water-containing solution is used as the solvent, an aqueous buffer may be added to form an aqueous buffer solution. The aqueous buffer solution is employed in the reaction to inhibit the formation of glycols during epoxidation. Aqueous buffers are well known in the art.

Aqueous buffers useful in this invention include any suitable salts of oxyacids, the nature and proportions of which in the mixture, are such that the pH of their aqueous solutions may range from 3 to 10, preferably from 4 to 9 and more preferably from 5 to 8. Suitable buffers include mixtures of phosphate, carbonate, citrate or borate anions with ammonium or alkali metal (e.g., Na, K, and Cs) cations. More preferred aqueous buffers include phosphate anions and most preferred are aqueous buffers consisting of mixtures of the monobasic and dibasic phosphates of sodium and/or potassium (e.g., $MH_2PO_4$ and $M_2HPO_4$, where M is $Na^+$ and/or $K^+$). Typically, the concentration of aqueous buffer in water is from about 0.0001 M to about 1 M, preferably from about 0.001 M to about 0.1 M, and most preferably from about 0.005 M to about 0.05 M.

Oxygen and hydrogen are also required for the process of the invention. Although any sources of oxygen and hydrogen are suitable, molecular oxygen and molecular hydrogen are preferred. The molar ratio of hydrogen to oxygen can usually be varied in the range of $H_2:O_2$=1:10 to 5:1 and is especially favorable at 1:5 to 2:1. The molar ratio of oxygen to olefin is usually 1:1 to 1:20, and preferably 1:1.5 to 1:10. Relatively high oxygen to olefin molar ratios (e.g., 1:1 to 1:3) may be advantageous for certain olefins.

In addition to olefin, oxygen and hydrogen, an inert gas carrier may be preferably used in the process. As the carrier gas, any desired inert gas can be used. Suitable inert gas carriers include noble gases such as helium, neon, and argon in addition to nitrogen and carbon dioxide. Saturated hydrocarbons with 1–8, especially 1–6, and preferably with 1–4 carbon atoms, e.g., methane, ethane, propane, and n-butane, are also suitable. Nitrogen and saturated $C_1$–$C_4$ hydrocarbons are the preferred inert carrier gases. Mixtures of the listed inert carrier gases can also be used. The molar ratio of olefin to carrier gas is usually in the range of 100:1 to 1:10 and especially 20:1 to 1:10.

Specifically in the epoxidation of propylene according to the invention, propane can be supplied in such a way that, in the presence of an appropriate excess of carrier gas, the explosive limits of mixtures of propylene, propane, hydrogen, and oxygen are safely avoided and thus no explosive mixture can form in the reactor or in the feed and discharge lines.

The amount of catalyst used may be determined on the basis of the molar ratio of the titanium contained in the titanium zeolite to the olefin that is supplied per unit time. Typically, sufficient catalyst is present to provide a titanium/olefin per hour molar feed ratio of from 0.0001 to 0.1.

For the liquid-phase process of the invention, the catalyst is preferably in the form of a suspension or fixed-bed. The process may be performed using a continuous flow, semi-batch or batch mode of operation. It is advantageous to work at a pressure of 1–100 bars. Epoxidation according to the invention is carried out at a temperature effective to achieve the desired olefin epoxidation, preferably at temperatures in the range of 0–250° C., more preferably, 20–200° C.

The following examples merely illustrate the invention. Those skilled in the art will recognize many variations that are within the spirit of the invention and scope of the claims.

EXAMPLE 1

Preparation of Au/TiO$_2$ CATALYST

Catalysts 1A and 1B: Chloroauric acid (0.25 g, Alfa Aesar) is dissolved in 400 mL of deionized water and the solution is heated to 70° C. The pH of the solution is then adjusted to pH 7.5 by the addition of 5% sodium hydroxide. Titania (10 g, Degussa P25) is added to the solution and the mixture is stirred for 1 hour before cooling to room temperature. The mixture is then filtered, and the solid is recovered and washed by stirring in 1 liter of deionized water for 10 minutes and then filtering the mixture. The recovered solid is then washed and filtered in the same manner 3 more times. The recovered solid is then dried under vacuum at room temperature for 12 hours, heated to 120° C. in air and held for 2 hours, and finally heated to 400° C. and held for 4 hours.

Catalyst 1C is prepared using the same method as described above, except that 0.75 gram of chloroauric acid is used.

EXAMPLE 2

Epoxidation of Propylene Using TS-1 and Au/TiO$_2$ Mixture

TS-1 can be made according to any known literature procedure. See, for example, U.S. Pat. No. 4,410,501, DiRenzo, et. al., *Microporous Materials* (1997), Vol. 10, 283, or Edler, et. al., *J. Chem. Soc., Chem. Comm.* (1995), 155. The TS-1 is calcined at 550° C. for 4 hours before use.

The catalyst mixture, containing TS-1 (1.5 g) and Au/TiO$_2$ (1.0 g), is slurried into 100 mL of water containing a buffer (0.01 molar MH$_2$PO$_4$+M$_2$HPO$_4$, M=2/1 K/Na) and added to the reactor system, consisting of a 300-mL quartz reactor and a 150-mL saturator. The slurry is then heated to 60° C. and stirred at 1000 rpm. A gaseous feed consisting of propylene, oxygen, hydrogen and the balance nitrogen is added to the system with a total flow of 100–460 cc/min and a reactor pressure of 15–90 psia. Both the gas and liquid phase samples are collected and analyzed by G.C.

Table 1 shows the reaction conditions for the epoxidation runs for Examples 2A–C. Example 2A uses Catalyst 1A, Example 2B uses Catalyst 1B, and Example 2C uses Catalyst 1C.

EXAMPLE 3

Epoxidation of Propylene Using TS-1 and Au/TiO$_2$ Mixture Without Aqueous Buffer Epoxidation is run according to the same procedure as Example 2 using catalyst 1B and TS-1, except that the water does not contain a buffer. Table 1 shows the reaction conditions.

TABLE 1

Reaction Conditions.

| Run # | Wt. % Au | Pressure (psia) | Feed Flow Rate (mL/min) | % Propylene in feed | % H2 in feed | % O2 in feed |
|---|---|---|---|---|---|---|
| 2A | 0.66 | 15 | 110 | 9 | 6 | 3 |
| 2B | 0.64 | 90 | 452 | 13 | 4 | 4 |
| 2C | 1.53 | 15 | 110 | 10 | 6 | 3 |
| 3  | 0.64 | 15 | 110 | 10 | 6 | 3 |
| 4* | —    | 15 | 110 | 9  | 6 | 3 |
| 5* | 0.64 | 15 | 110 | 11 | 6 | 3 |

*Comparative Example

TABLE 2

Epoxidation Results.

| Run # | PO (%) | PG[1] (%) | DPG[2] (%) | Acetol (%) | HOAc (%) | CO$_2$ (%) | Propane (%) | PO/RO[3] | POE Productivity (g POE/g cat-h) |
|---|---|---|---|---|---|---|---|---|---|
| 2A | 79.4 | 10   | 3.1 | 2.6 | 4.8 | 0   | 0   | 3.9 | 0.0013 |
| 2B | 75.2 | 19.9 | 0   | 1.1 | 0   | 0   | 3.9 | 3.6 | 0.0039 |
| 2C | 63.9 | 32   | 0   | 2.7 | 1.3 | 0.1 | 0   | 1.8 | 0.0016 |
| 3  | 24.1 | 72.1 | 0   | 3.6 | 0   | 0.2 | 0   | 0.3 | 0.0027 |
| 4* | —    | —    | —   | —   | —   | —   | —   | —   | 0 |
| 5* | —    | —    | —   | —   | —   | —   | —   | —   | 0 |

*Comparative Example.
[1]PG = propylene glycol
[2]DPG = dipropylene glycol
[3]RO = Ring-Opened Products.

COMPARATIVE EXAMPLE 4

Epoxidation of Propylene Using TS-1 Only

Epoxidation with TS-1 only (1.5 g) is run according to the same procedure as Example 2. Table 1 shows the reaction conditions.

COMPARATIVE EXAMPLE 5

Expodation of Propylene Using Au/TiO$_2$ Only

Epoxidation with Au/TiO$_2$ only (1.0 g) is run according to the same procedure as Example 2. Table 1 shows the reaction conditions.

The epoxidation results (see Table 2) show that the use of a catalyst mixture of TS-1 and Au/TiO$_2$ leads to the production of propylene oxide (PO) and PO equivalents ("POE") in the epoxidation of propylene with H$_2$ and O$_2$. This result is surprising given the fact that TS-1 or Au/TiO$_2$ alone do not produce propylene oxide under the same conditions.

I claim:

1. A process for producing an epoxide comprising reacting an olefin, hydrogen and oxygen in an oxygenated solvent in the presence of a catalyst mixture comprising a titanium zeolite and a supported catalyst comprising gold and a support, wherein the support is an inorganic oxide containing titanium or zirconium.

2. The process of claim 1 wherein the titanium zeolite is titanium silicalite.

3. The process of claim 1 wherein the titanium zeolite is TS-1.

4. The process of claim 1 wherein the supported catalyst is comprised of from 0.01 to 10 weight percent gold.

5. The process of claim 1 wherein the support is titania, zirconia, or titania-silica.

6. The process of claim 1 wherein the olefin is a C$_2$–C$_6$ olefin.

7. The process of claim 1 wherein the olefin is propylene.

8. The process of claim 1 wherein the oxygenated solvent is selected from the group consisting of water, C$_1$–C$_4$ alcohols, and mixtures thereof.

9. The process of claim 8 wherein the oxygenated solvent is water.

10. The process of claim 8 wherein the oxygenated solvent contains an aqueous buffer.

11. The process of claim 1 further comprising a carrier gas.

12. The process of claim 11 wherein the carrier gas is selected from the group consisting of helium, neon, argon, nitrogen, carbon dioxide, and $C_{1-8}$ saturated hydrocarbons.

13. The process of claim 11 wherein the carrier gas is propane.

* * * * *